US006461311B2

(12) United States Patent
DuBois et al.

(10) Patent No.: US 6,461,311 B2
(45) Date of Patent: Oct. 8, 2002

(54) LOW FRICTION GUIDEWIRE WITH OFF-CENTER CORE

(75) Inventors: Tom DuBois; Richard Elton, both of Glens Falls, NY (US); Gary Teague, Conyers, GA (US)

(73) Assignee: C.R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 09/784,578

(22) Filed: Feb. 15, 2001

(65) Prior Publication Data

US 2001/0009981 A1 Jul. 26, 2001

Related U.S. Application Data

(63) Continuation of application No. 09/257,425, filed on Feb. 25, 1999.
(60) Provisional application No. 60/076,785, filed on Mar. 4, 1998.

(51) Int. Cl.$^7$ .................................................. A61B 5/00
(52) U.S. Cl. ........................................................ 600/585
(58) Field of Search ................................ 600/434, 435, 600/585

(56) References Cited

U.S. PATENT DOCUMENTS

| | | | |
|---|---|---|---|
| 4,003,369 A | 1/1977 | Heilman et al. | 128/2 M |
| 4,748,986 A | 6/1988 | Morrison et al. | 128/772 |
| 4,854,330 A | 8/1989 | Evans, III et al. | 128/772 |
| 4,925,445 A | 5/1990 | Sakamoto et al. | 604/95 |
| 5,067,489 A | 11/1991 | Lind | 128/772 |
| 5,077,352 A | 12/1991 | Elton | 525/409 |
| 5,084,022 A | 1/1992 | Claude | 604/164 |
| 5,160,790 A | 11/1992 | Elton | 428/412 |
| 5,179,174 A | 1/1993 | Elton | 525/409 |
| 5,213,111 A | 5/1993 | Cook et al. | 128/772 |
| 5,251,640 A | 10/1993 | Osborne | 128/772 |
| 5,290,585 A | 3/1994 | Elton | 427/2 |
| 5,333,620 A | 8/1994 | Moutafis et al. | 128/772 |
| 5,373,856 A | 12/1994 | Grenouillet | 128/772 |
| 5,433,200 A | 7/1995 | Fleischhacker, Jr. | 128/657 |
| 5,452,726 A | 9/1995 | Burmeister et al. | 128/772 |
| 5,749,837 A | 5/1998 | Palermo et al. | 600/585 |
| 5,797,857 A | 8/1998 | Obitsu | 600/585 |

FOREIGN PATENT DOCUMENTS

| | | | | |
|---|---|---|---|---|
| EP | 0 405 823 | 1/1991 | | A61M/25/01 |
| EP | 0 454 293 | 10/1991 | | C08G/18/10 |
| EP | 0 744 186 | 11/1996 | | A61M/25/01 |

Primary Examiner—Max Hindenburg
(74) Attorney, Agent, or Firm—Darby & Darby

(57) ABSTRACT

A flexible, kink-resistant, low-friction guidewire for positioning a medical instrument through tortuous passageways within a patient is disclosed. The guidewire includes a core wire which remains substantially free of any residual strain when it is positioned within the patient, a metal coil about the core wire and extending substantially the entire length of the core, a primer coating on the coil and a hydrophilic, lubricous coating on the primer coating. The core wire is preferably a superelastic metal alloy such as Nitinol. The metal coil is preferably formed from a wire with a rectangular cross section. The primer is preferably one which reacts with species of isocyanate or hydroxyl, and the hydrophilic, lubricous coating is preferably a cross-linked polymer selected from the group of polyurethane, polyurea, and polyurethaneurea, complexed with a hydrophilic complexing species such as poly(ethylene oxide) or polyvinylpyrrolidone. A method for manufacturing and coating such a guidewire is also disclosed.

30 Claims, 1 Drawing Sheet

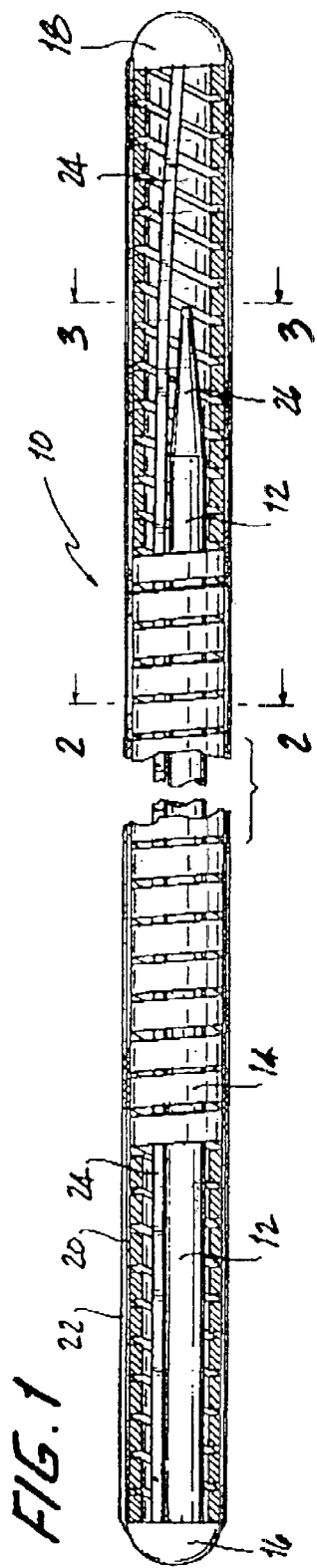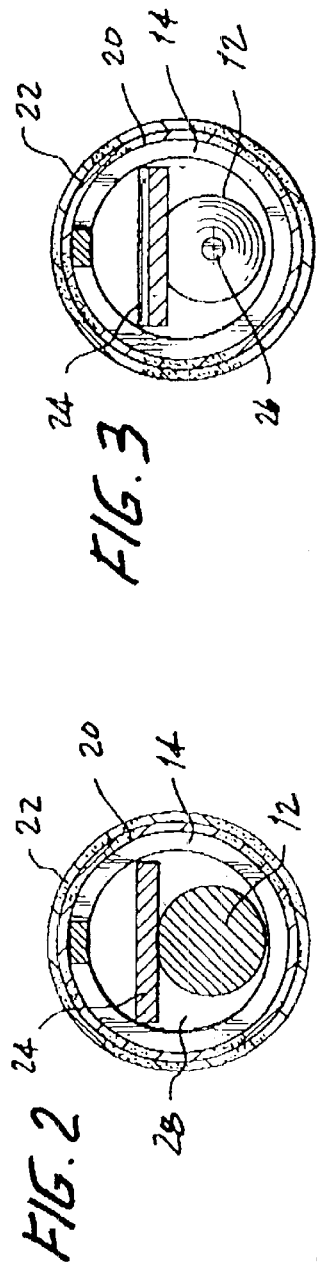

LOW FRICTION GUIDEWIRE WITH OFF-CENTER CORE

This application is a continuation of application Ser. No. 09/257,425, filed Feb. 25, 1999, which claims benefit of Provisional application Ser. No. 60/076,785, filed Mar. 4, 1998.

FIELD OF THE INVENTION

This invention relates to guidewires for use in surgical procedures and more particularly to a flexible kink resistant, low friction, coated guidewire having a formable tip, and a method for making same.

BACKGROUND OF THE INVENTION

Elongated, flexible guides are often used in medical procedures to gain access to specific internal sites within the body without major surgery. Guides are advanced through the body, for example, through peripheral blood vessels, the gastrointestinal tract, or the urinary tract. Guides, often referred to as guidewires, are commercially available and are currently used, among other fields, in cardiology, electrophysiology, gastroenterology, urology, and radiology.

Once positioned indwelling, the guidewire defines the path for the introduction of catheters and other medical instruments to a desired site; however, such instruments are generally less wieldy than the guidewire, have significantly more mass, and create a risk of kinking the guidewire as they are, advanced over the guidewire.

Typical guidewire constructions include a central core wire made of stainless steel or other metal which provides stiffness to the guidewire, and have a distal or forward end portion of increased flexibility to better enable the clinician to maneuver the guidewire into the appropriate passageway. The more proximal portion of the guidewire provides the requisite stiffness to support and guide the medical instrument to the site accessed by the guidewire. Depending on the design, the guidewire may include a coil along the distal portion of the guidewire, or which surrounds the entire core wire. Also, in some designs, the core wire is movable within the coil to permit the clinician to selectively adjust the flexibility of the guidewire as the guidewire is being positioned and while a catheter or other instrument is being advanced thereover. In designs which include a coil, a distal weld is commonly made at the distal end of the coil to provide an atraumatic tip, and a safety wire welded to the tip extends proximally, within the coil, to better ensure that the tip does not separate from the guidewire during use.

In most designs, the dimension of the core wire essentially defines the stiffness of the guide wire along its length. For a given core wire material, the greater its cross-section, the greater the stiffness of the overall guidewire. The choice of core wire material affects the performance characteristics of the guidewire, as well as its cost. Core wires made of stainless steel are inexpensive, but are prone to kinking s during advancement of catheters and other instruments. Core wires made of fiberglass composites are more resistant to kinking but they are more prone to abruptly snapping, and it is difficult to provide a taper to the distal end of the fiberglass core, to improve its flexibility, without splintering. See U.S. Pat. No. 5,251,640 of Osborne. Core wires made of shape memory alloys that have been processed to be superelastic at body temperature remain expensive. Further, superelastic guidewires do not readily take a set, for example, a J-shaped tip or a hockey-stick tip, but rather require further process steps to render the tip portion non-superelastic.

U.S. Pat. No. 4,925,445 of Sakamoto et al., discloses a guidewire construction which includes a superelastic core wire surrounded by a thick polymer jacket. The jacket design builds up the thickness of the guidewire to the desired dimension without the need for a superelastic core wire that is substantially the same diameter as the overall outer diameter of the guidewire. A guidewire where the core wire was substantially the same diameter as the overall diameter of the diameter of the guidewire would be insufficiently flexible for some intended applications. The polymer jacket is expensive to apply, and is typically added by an over extrusion process, by heat shrinking tubing over the core wire, or by hot sizing the jacket material. Another problem with jacketed guidewire designs is that the dimensionally significant jacket placed over the core wire may obscure the performance characteristics of the core wire itself. Therefore, there remains a need for a design to build up the outer diameter, while allowing appropriate flexibility of the product.

To promote ease of insertion, withdrawal, and positioning of the guidewire, it is generally desirable to provide guidewires with a hydrophilic, lubricious outer surface. There are difficulties associated with hydrophilic, lubricous coatings applied directly to a metal coil. Such coatings have generally only been applied to polymer jacketed guide wires. Typically, the hydrophilic lubricous coating is a hydrogel material, and as such, when it is hydrated, it absorbs a significant amount of water, swells, and loses adhesion to the steel.

A desirable improvement in the art would be a flexible, low cost, kink resistant, low friction guidewire having a formable tip.

SUMMARY OF THE INVENTION

The present invention provides a lower cost, flexible, kink-resistant, low-friction guidewire for positioning a medical instrument through tortuous passageways within a patient. The guidewire includes a core wire which is positionable within the patient substantially free of any residual strain, a metal coil about the core wire and extending substantially the entire length of the core, a primer coating on the coil and a hydrophilic, lubricous coating on the primer coating. The primer is preferably one which reacts with species of isocyanate or hydroxyl, and the hydrophilic, lubricous coating is preferably a cross-linked polymer selected from the group of polyurethane, polyurea, and polyurethaneurea, complexed with a hydrophilic complexing species such as poly(ethylene oxide) or polyvinylpyrrolidone.

The present invention also provides a method for manufacturing and coating a guide wire of various constructions, and includes the steps of applying a polymer primer to the guide wire, applying a hydrophilic layer over the primer, and permitting the hydrophilic, lubricous layer to bond with the polymer primer and cure. In a preferred embodiment the primer reacts with species of isocyanate or hydroxyl, and the hydrophilic, lubricous layer is a cross-linked polymer complexed with a hydrophilic complexing species.

These and other features and objects of the invention are more fully appreciated from the unscaled drawings and the following detailed description of a preferred embodiment of the invention.

BRIEF DESCRIPTION OF THE DRAWINGS

FIG. 1 illustrates a top plan view, partially broken-away, of a guide according to a preferred embodiment of the invention;

FIG. 2 illustrates a cross-sectional view, taken along lines 2—2 of FIG. 1;

FIG. 3 illustrates a cross-sectional view, taken along lines 3—3 of FIG. 1; and

FIG. 4 illustrates a side view, in section, of the guidewire of FIG. 1 having a moveable core wire.

DETAILED DESCRIPTION OF A PREFERRED EMBODIMENT

By way of overview and introduction, FIG. 1 illustrates a guide wire 10 according to a preferred embodiment of the invention. The guidewire 10 has an elongated, tapered core wire 12, a spring coil 14 about the core wire which extends between a proximal end 16 of the guidewire to its distal end 18, a primer layer 20, a hydrophilic, lubricous coating 22 disposed over at least a portion the coil and perhaps the entire coil, and a safety wire 24 extending from the spring coil proximal end 26 to the guidewire distal tip 18.

In accordance with a salient aspect of the invention, a superelastic core wire 12 having a desired stiffness is disposed within a stainless steel spring coil 14. The spring coil is attached to a stainless steel safety wire 24 and to at least the distal weld 18 to add structural integrity, without the need for bonding the dissimilar materials of the spring coil 14 and the core wire 12. The winding wire of the spring coil 14 has a diameter or thickness selected to allow an appropriate overall outside diameter of the guidewire 10, one which is substantially the same its finished diameter. A thin or dimensionally insignificant primer 20 is applied directly to at least the outside surface of the coil 14, and a thin or dimensionally insignificant hydrophilic, lubricous coating 22 is applied to the primer 20. Such thin coatings differ from resin envelopes which have been provided in prior art designs such as in U.S. Pat. No. 5,797,857 of Obitsu to provide a smooth outer surface by filling voids and area along the outer surface.

The core wire 12 preferably is made of a shape memory alloy which exhibits superelastic/pseudoelastic shape recovery characteristics when positioned through tortuous passageways of a patient. Such an alloy can undergo significant bending as the guidewire 10 is advanced through, for example, a coronary arterial system, without kinking or being reshaped. That is, it can be positioned and subsequently withdrawn substantially free of any residual strain. A suitable shape memory alloy exhibits superelasticity from 15° C. to about 37° C. and above, and at least throughout a range of temperatures between operating room temperatures (20°–22° C.) and body temperature (37° C.). Such alloys are known in the field and are characterized by their ability to undergo substantial bending in response to stress with little to no residual strain when the stress is removed. Alternatively, a cold-worked martensitic microstructure can be used to provide enhanced shape recovery and a lower stiffness, than, for example, stainless steel. A preferred nitinol alloy composition which exhibits superelasticity in the requisite temperature range has about 55 to about 56 wt. % nickel and the remainder titanium, and is commercially available in wire form of, for example, 10 to 30 mil, and also in the narrower and more common sizes of 16 to 24 mil. Trace tertiary elements may be present in the alloy, and their amounts can be varied to shift the transformation temperatures to an appropriate temperature to ensure that the finished core wire 12 is completely austenitic at body temperature. The core wire 12, however, can be made out of other springy metal material such as stainless steel and the like.

Two examples of suitable nitinol alloys and wire sizes have the following dimensions, chemical compositions (in wt. %), and material characteristics, respectively:

| 21 mil wire | | 24 mil wire | |
|---|---|---|---|
| Ni | 55.77 | Ni | 55.99 |
| Ti | 44.18 | Ti | 43.99 |
| C | 0.5 max | C | 0.5 max |
| Mn | <0.01 | Mn | <0.01 |
| Si | <0.01 | Si | <0.01 |
| Cr | <0.01 | Cr | <0.01 |
| Mo | <0.01 | Mo | <0.01 |
| Fe | <0.05 | Fe | <0.05 |
| Al | <0.01 | Al | <0.01 |
| Cu | <0.01 | Cu | <0.01 |
| Co | <0.01 | Co | <0.01 |
| O | 0.05 max | O | 0.05 max |
| Tensile Strength = | 220,000 PSI | Tensile Strength = | 209,000 PSI |
| Breaking Load = | 75.3 Lbs. | Breaking Load = | 94.6 Lbs. |
| Elongation = | 15% | Elongation = | 15% |

Shape memory alloys are preferred because of their capacity to elastically recover almost completely to an initial configuration. That is, shape memory alloys have the capacity to avoid taking a "set" when deformed; in this manner, a guide wire of the invention having a core wire 12 of shape memory alloy may be substantially straight when unstressed, may elastically deform as it passes through curved body channels, and yet will recover its straight configuration when stress is removed. Using a calibrated micrometer and also a calibrated dial caliper, initially straight 21 mil and 24 mil core wires of the above composition were bent 450° about a pin to determine the minimum bend radius to which the core wire can be subjected without appreciable residual strain. The results of those measurements are shown below.

| Pin Radius | 21 mil wire | 24 mil core wire |
|---|---|---|
| 0.53" | no residual strain | no residual strain |
| 0.41" | no residual strain | very slight res. strain |
| 0.37" | no residual strain | ≈3° residual deflection |
| 0.31" | no residual strain | ≈3° residual deflection |
| 0.25" | no residual strain | ≈6° residual deflection |
| 0.16" | slight residual deflection (≈1°) | ≈7° residual deflection |
| 0.14" | ≈4° residual deflection | ≈12° residual deflection |
| 0.10" | ≈13° residual deflection | ≈27° residual deflection |

The measurements show that a thinner diameter core wire can be bent to a tighter bend radius than a thicker diameter core wire. The 21 mil. core wire can be bent about a 0.25" bend radius with no residual strain, and the 24 mil core wire can be bent about a 0.41" bend radius with only a very slight residual strain which is too small to quantify, and which is less than 1°.

To enable the distal portion of the guidewire to be formed into a curve, if desired, the safety wire 24 is formable. The curve shape facilitates advancement of the guidewire 10 into side or peripheral branches of any body passageway. The safety wire 24 extends within the coil 14, along with the core wire 12, and is attached at its distal end to the outer spring coil 14 at the distal weld 18. For an angiographic guidewire having an outer diameter of 35 mil, the safety wire 24 preferably comprises a 3 mil by 10 mil rectangular wire, but may be larger or smaller depending on the stiffness required (which in turn depends on the diameter of the core wire 12), the product tensile characteristics required, and the diameter of the lumen 28 defined by the winding wire of the coil 14. Other shaped wires, such as circular cross section wires, may also be used for the safety wire.

As illustrated in FIG. 2, the core wire 12 and rectangular safety wire 24 reside off-center within the lumen 28 of the coil 14. The safety wire 24 is attached at its proximal end typically by a resistance weld 30 (see FIG. 4) to the proximal end of the coil 14 and, optionally, to the proximal weld 16 in a fixed core wire 12 construction.

With further reference to FIGS. 1 and 2, the coil 14 is an elongated, helically wound wire coil which preferably has a rectangular cross section (a flat winding wire), as shown in the drawing, but can have a circular cross section instead (for example, about 5 mil to about 7 mil in diameter). A flat winding wire provides the clinician with a smoother surface as the guidewire is advanced through the passageway and as instruments are advanced thereover, and provides a larger lumen 28. The spring coil provides an increase in the outer diameter to substantially the outer diameter of the finished product. The spring coil 14 extends substantially the entire length of the guidewire 10, beyond the tapered core wire tip 26, and is attached to the distal weld 18, and to the proximal weld 16 in fixed core guidewire constructions. The proximal weld eliminates the need to solder or braze the safety wire 24 to the superelastic core wire 12. Preferably, the coil 14 is a metal wire such as stainless steel. The coil 14 imparts flexibility to the forward tip of the guidewire 10, and substantially maintains the outer diameter of the guidewire throughout the length of the guidewire, including the tapering core wire tip 26 (see FIG. 3). A preferred winding wire for the coil 14 is a rectangular winding wire 4 mil by 8 mil in cross-section. Such a winding wire increases the overall cross-section of the guidewire 10 to a diameter that can be readily handled by the clinician without the need for a wider core wire 12. Also, for many common guidewire sizes, such as 35 mil outer diameter, a core wire substantially the same outer diameter as the finished product would render the product inappropriately stiff for many of the intended applications. An angiographic guidewire, for example, having a typical outside diameter of 35 to 38 mil, can house a core wire 12 having 24 mil or less thickness (or diameter), for example, along with the typically rectangular safety wire 24. Further, by using the coil 14 to increase the overall diameter of the guidewire 10 to the desired outside diameter, the primer 20 and coating 22 can be very thin (e.g., ≈<0.001") as compared to the cross-section of the coil 14 and the core wire 12.

The primer 20 is applied over at least some of the length of the coil 14 up to the entire length of the coil on at least the outside surface of the coil, and serves as a base for adhering the hydrophilic coating 22 to the stainless steel coil 14, and prevents the coating from separating when it hydrates with water, by way of a chemical bond, chemical infusion bond, or mechanical bond. Examples of primer materials include, but are not limited to, thermoplastic, solvent soluble polymers or dispersable polymers such as polyurethanes, polyamides, poluvinylchloride (PVC), and polyesters. Also, suitable primer materials may include cross-linkable materials which react to form a cross-linked polymer film, such as cross-linked polyurethanes, alkyd resins, and cross-linked polyesters.

In the preferred embodiment, the primer 20 contains functional groups that react with species of either hydroxyl or is isocyanate that are present in the preferred hydrophilic coating 22, namely, a cross-linked polymer, selected from the group of polyurethane, polyurea, and polyurethaneurea complexed with either a high molecular weight poly (ethylene oxide) or a polyvinylpyrrolidone ("PVP"), that is, a species having a molecular weight greater than about 10,000. Examples of primers which contain such reactive functional groups include, but are not limited to, polyurethanes, polyamides, polyvinylbutyral, polyisocyanates, isocyanate prepolymers, polyureas, polyerethaneureas, polyvinylalcohols, polyvinylalcohol copolymers, polyetherpolyamide copolymers, and blends of these with each other, or with other polymers.

In the preferred embodiment, the cross-linked matrix of the coating 22 complexes a water soluble polymer. Such coatings are of the types discussed in U.S. Pat. Nos. 5,077,352, 5,179,174, 5,290,585 and 5,160,790 of Elton, the disclosures of which are hereby incorporated by reference as if set forth in their entireties herein. Such a coating does not require an osmolality increasing compound, because it is stable over time (that is, no component of hydrophilic coating leaches out) and is therefore less complicated-to apply than coatings which require an osmolality increasing compound. Other examples of hydrophilic coatings include, but are not limited to, the following: (a) thermoplastic, solvent soluble hydrophilic polymers; (b) hydrophilic coatings formed as a reaction between a reactive base coating material, such as an isocyanate prepolymer, and a hydrophilic top coating material, such as PVP, poly(ethylene oxide) or polyvinyl alcohol; and (c) solvent soluble, or solvent dispersable blends of a thermoplastic material such as polyurethanes, cellulose esters, polyvinylbutyrol or polyesters, and a water soluble polymer such as PVP, poly(ethylene oxide) or polyvinyl alcohol. There are also other types of hydrophilic coating systems which are known to those skilled in the art.

Suitable hydrophilic polymer coatings 22 imbibe a significant amount of water on a weight basis, for example, greater than 50% its own weight and especially greater than 100% its own weight. In the preferred embodiment, by complexing the cross-linked polymer with poly(ethylene oxide) or PVP, the coating becomes hydrophilic, and dissolution of the hydrophilic polymer is prevented when the coating imbibes water. This is because the cross-linked polymer has a network of covalent bonds which form a network structure and result in a durable matrix, as compared to a non-cross-linked polymer.

The coating 22 is applied over the polymeric primer layer, over at least the distal portion of the guidewire 10, extending proximally toward and possibly including the proximal end of the coil 14. The primer 20 and coating 22 can be applied using any conventional method known to those of ordinary skill in the art, including dipping, spray coating and die wiping, and typically need only have a thickness of about 1 mil or less. A further description of these known techniques is available in the relevant literature.

FIG. 4 illustrates a guidewire 10' having a moveable core wire 12'. The other elements are the same as illustrated in the preceding figures and have been denoted with the same reference numbers. The core wire 12' is a superelastic core wire as in FIG. 1, and preferably has a handle or grasp 16' at its proximal tip (for example, a piece of shrink tubing or a grip attached to the core wire proximal end). The core wire distal tip 26' is provided with a radiused tip to ease advancement and to prevent inadvertent perforation of the coil 14 upon advancement of the core wire 12' within the guidewire 10'. The movable core 12' can be retracted proximally to increase the flexibility of the distal end of the guidewire, and re-inserted to provide column support for a catheter to be advanced thereover. The safety wire 24 is attached to the guidewire distal end at the distal weld 18 and at the guidewire proximal end at the weld 30. As in FIG. 1, the guidewire 101 includes the primer 20 and hydrophilic, lubricous coating 22.

While a circular core wire 12, 12' has been illustrated, other configurations could be used with equal advantage, including core wires having rectangular or square cross sections. Further, a tapered core wire will have a predetermined stiffness at various locations along its length which are dictated, in part, by the intended application. There may be one or more transitions (e.g., steps) from one diameter to another along the length of the core wire, with a different predetermined stiffness associated with the core segment after each such transition.

While a preferred embodiment of the present invention has been described, it should be understood that various changes, adaptations and modifications may be made therein without departing from the spirit of the invention and the scope of the appended claims.

What is claimed is:

1. A guide wire for positioning a medical instrument through tortuous passageways within a patient, comprising:
    a flexible core wire which remains substantially free of any residual strain when positioned within the patient;
    a metal coil enveloping the core wire for substantially its entire lengths,
    the core wire being positioned off-center within the coil;
    a primer coating on the metal coil; and
    a hydrophilic, lubricous coating disposed over the primer coating.

2. The guide wire as in claim 1, wherein the primer is a polymer that reacts with species of isocyanate or hydroxyl.

3. The guide wire as in claim 2, wherein the hydrophilic, lubricous coating is a cross-linked polymer complexed with a hydrophilic complexing species.

4. The guide wire as in claim 3, wherein the cross-linked polymer is selected from the group of polyurethane, polyurea, and polyurethaneurea.

5. The guide wire as in claim 3, wherein the hydrophilic complexing species has a molecular weight greater than 10,000.

6. The guide wire as in claim 3, wherein the hydrophilic complexing species is one of poly(ethylene oxide) and a polyvinylpyrrolidone.

7. The guide wire as in claim 3, wherein the hydrophilic, lubricous coating is free of an osmolality increasing compound.

8. The guide wire as in claim 1, wherein the hydrophilic, lubricous coating is a cross-linked polymer complexed with a hydrophilic complexing species.

9. The guide wire as in claim 8, wherein the cross-linked polymer is selected from the group of polyurethane, is polyurea, and polyurethaneurea.

10. The guide wire as in claim 8, wherein the hydrophilic complexing species is one of poly(ethylene oxide) and a polyvinylpyrrolidone.

11. The guide wire as in claim 1, wherein the metal coil is made from a wire having a rectangular cross section.

12. The guide wire as in claim 1, wherein the coil has a proximal end and a distal end, and further comprising an elongated safety wire extending between proximal and distal ends of the coil.

13. The guidewire as in claim 1, wherein the core wire has a tapering distal segment.

14. The guide wire as in claim 1, wherein the core wire terminates proximal to the distal end of the coil.

15. The guidewire as in claim 1, wherein the core wire terminates in a radiused tip and has a substantially constant diameter along its length.

16. The guidewire as in claim 1, wherein the core wire is movable relative to the metal coil.

17. The guide wire as in claim 16, wherein the primer is a polymer that reacts with species of isocyanate or hydroxyl.

18. The guide wire as in claim 1, wherein the primer is a polymer that reacts with species of isocyanate or hydroxyl, the hydrophilic, lubricous coating is a cross-linked polymer complexed th a hydrophilic complexing species, the cross-linked polymer being selected from the group of polyurethane, polyurea, and polyurethaneurea, and the hydrophilic complexing species being one of poly(ethylene oxide) and polyvinylpyrrolidone.

19. The guide wire as in claim 1, wherein the hydrophilic coating is one of a thermoplastic solvent soluble material and a thermoplastic solvent dispersable material.

20. The guide wire as in claim 1, wherein the hydrophilic coating is one of a solvent soluble and a solvent dispersable blend of a stabilizing polymer and a hydrophilic material.

21. The guide wire as in claim 1, wherein the hydrophilic coating comprises a first layer being a reactive base coat and a second, outer layer being a hydrophilic material.

22. The guide wire as in claim 1, wherein the coil has a proximal end and a distal end, wherein both the primer and the hydrophilic coating terminate distal to the proximal end of the coil, the proximal end of the coil being uncoated.

23. The guidewire as in claim 1, wherein a portion of the primer is not covered with the hydrophilic coating.

24. The guide wire as in claim 1, wherein the core wire is made from one of the group consisting of steel and a superelastic alloy.

25. The guide wire as in claim 1, further comprising a safety wire fixedly positioned relative to the coil.

26. The guide wire as in claim 25, wherein the off-center core wire abuts both the safety wire and the coil.

27. The guide wire as in claim 25, wherein the safety wire is formable.

28. A method for producing a flexible, kink resistant, lubricious guidewire suitable for an intended application, comprising the steps of:
    providing an elongated superelastic core wire having a predetermined stiffness at preselected locations along its length;
    disposing a helically wound metal coil about the entire length of the core wire with the core wire being positioned off-center within the coil, the coil increasing the overall diameter of the guidewire to substantially a preselected diameter providing additional stiffness there to such that the core wire and coil assembly possess a stiffness suitable for the intended application;
    applying a polymeric primer layer to the exterior of at least a portion of the helically wound metal coil; and
    applying a hydrophilic, lubricious coating layer over at least a portion of the primer layer.

29. A method as in claim 28, including the additional step of extending a safety wire substantially the full length of the coil within the coil and affixing the safety wire to at least the proximal and distal ends of the coil.

30. A method as in claim 29, wherein the safety wire is affixed to the helically wound coil by a welding process.

* * * * *